United States Patent [19]

Garcia

[11] Patent Number: 5,717,997
[45] Date of Patent: Feb. 17, 1998

[54] HIP PAD FOR PROTECTING GREATER TROCHANTER FROM IMPACT

[75] Inventor: Mario C. Garcia, West St. Paul, Minn.

[73] Assignee: Prevent Products, Inc., West St. Paul, Minn.

[21] Appl. No.: 596,730

[22] Filed: Feb. 5, 1996

Related U.S. Application Data

[63] Continuation of Ser. No. 239,537, May 9, 1994, abandoned.

[51] Int. Cl.$^6$ .................................................. A41D 13/00
[52] U.S. Cl. ............................................ 2/23; 2/465
[58] Field of Search ................... 2/22, 23, 24, 455

[56] References Cited

U.S. PATENT DOCUMENTS

| | | |
|---|---|---|
| 835,219 | 11/1906 | Flick . |
| 1,088,273 | 2/1914 | Golden . |
| 1,527,009 | 2/1925 | Plate . |
| 2,889,830 | 6/1959 | Raymond . |
| 3,772,704 | 11/1973 | Carbonneau . |
| 3,909,847 | 10/1975 | Holt et al. . |
| 4,177,806 | 12/1979 | Griffin . |
| 4,272,850 | 6/1981 | Rule . |
| 4,479,269 | 10/1984 | Balliet . |
| 4,573,216 | 3/1986 | Wortberg . |
| 4,641,641 | 2/1987 | Strock . |
| 4,748,975 | 6/1988 | Yashima . |
| 4,807,301 | 2/1989 | Ferber . |
| 5,014,354 | 5/1991 | Dumont . |
| 5,020,547 | 6/1991 | Strock . |
| 5,105,473 | 4/1992 | Valtakari . |
| 5,134,726 | 8/1992 | Ross . |
| 5,220,691 | 6/1993 | Wiegers . |
| 5,309,570 | 5/1994 | Grimm . |
| 5,410,756 | 5/1995 | Hutson . |

OTHER PUBLICATIONS

Wallace et al., "Iowa FICSIT Trial: The Feasibility of Elderly Wearing a Hip Joint Protective Garment to Reduce Hip Fractures", *JAGS*, Mar. 1993, vol. 41, No. 3, pp. 338–340.

Robb III, "Hip fracture disease: Coping with a contemporary epidemic", The Journal of Musculoskeletal Medicine, Dec. 1993, pp. 12–16 and 23–24.

*Primary Examiner*—Paul C. Lewis
*Attorney, Agent, or Firm*—Haugen and Nikolai, P.A.

[57] ABSTRACT

A form-fitting garment having side pockets that allow hip pads for the protection of the greater trochanter, to be securely positioned and centered above the greater trochanter region is described. The hip pads have a slit extending through the planar surface that is centered over the greater trochanter region and disperses any impact forces against the pad away from the greater trochanter region.

6 Claims, 2 Drawing Sheets

HIP PAD FOR PROTECTING GREATER TROCHANTER FROM IMPACT

This is a Continuation of application Ser. No. 08/239,537, filed on May 9, 1994, now abandoned.

BACKGROUND OF THE INVENTION

I. Field of the Invention

This invention relates generally to a garment with a protective pad for the hip joint area. More particularly, it relates to a force dissipating energy absorbent hip pad for use in geriatric patients protection of the greater trochanter from impact and ultimate creation of fractures.

II. Discussion of the Prior Art

At a time when health care costs are escalating, medical research continues to focus on preventative medicine. The study of geriatrics has revealed that elderly individuals have an increased risk of hip fractures and deaths related to hip fracture disease. Included within the elderly group are several groups at greater risk. Among some of these greater at-risk groups are: persons, particularly females, over age 50, persons with chronic medical conditions, persons with impaired acuity, persons with osteoporosis, and persons with bodies having low muscle/fat content. The most frequent cause of hip fractures results from a fall, including light falls.

In the past, various devices have been constructed to prevent hip injuries. These devices include hip pads used by athletes while playing soccer, hockey, baseball and also by skiers. Devices have also been constructed to prevent such injury among the elderly. These devices often contain a recess in the pad that must be aligned in position directly above the greater trochanter region. These pads have been taped or strapped in place causing slight discomfort to the elderly person. When strapped in place, the pads have a tendency to slip becoming misaligned with the greater trochanter. The slipped pads decrease the effectiveness of protecting the greater trochanter from fractures. Further, these devices are often difficult to place in position directly surrounding the greater trochanter area. Medical assistance may be required to properly position and secure the pad to the hip. Also, the present hip pads are manufactured in a variety of sizes, increasing the costs of manufacture.

SUMMARY OF THE INVENTION

It is accordingly a principal object of the present invention to provide a comfortable, self-centering and user-friendly garment with a hip pad for use in geriatric patients for protection of the greater trochanter from impact and ultimate hip fracture problems.

Another object of the present invention is to provide a self-fitting garment that retains the hip pad in place in the general region of the greater trochanter.

Yet, another object of the present invention is to provide a flexible, self-centering, energy-absorbent hip pad that dissipates and spreads an impact force away from the greater trochanter region.

A further object of the present invention is to provide an energy-absorbent hip pad that is easy to use and does not require medical assistance to properly position the pad.

A still further object of the present invention is to provide an energy-absorbent hip pad with ventilation to allow the hip pad to dissipate absorbed heat.

In accordance with the present invention, the foregoing objects and advantages are achieved by providing a form-fitting garment that contains a molded, flexible planar member (hip pad) of predetermined geometric shape, with a cross-slit extending through the thickness of the hip pad.

The hip pad may be constructed with a plurality of slots that allows for a certain amount of shifting of the garment without compromising the effectiveness of the hip pad, and without creating a stress point in the pad directly over and/or surrounding the area of the greater trochanter. The garment may be worn underneath other clothing or may be fashioned to be worn as outer apparel. On each side of the garment is a pocket for retaining the hip pad. The pocket may be made of the same material as the overall garment but must have a certain degree of resilience to hold the hip pad in the same relative position within the pocket while being worn.

The form-fitting garment allows the pads to be properly positioned without requiring adhesives or straps, thereby making the application of this protection comfortable to the user. Further, because the protection is within the garment and is-self-positioning, the user may be slightly disoriented and yet be able to properly arrange the protective garment in place. The form-fitting garment may be proportioned in various sizes to accommodate various configurations of the human body while utilizing the same hip pad. The pads conform to the individual's body structure thereby creating a comfortable fit.

The form-fitting garment, with properly positioned pockets, retains the hip pads in the same relative position with respect to the hip. In this manner, each hip pad is centered over and surrounds the greater trochanter region. The cross slit mid-point is preferably centered over the apex of the greater trochanter. The slits extend through the hip pad and redirect energy from an impact away from the area directly above the greater trochanter. In this manner, the hip pad aids in dissipation of the impact forces, and absorbs and redirects some of the energy from these forces away from the greater trochanter. Thus, by wearing the garment, some injury and some possible hip fractures are avoided.

When worn, the hip pad of the hip pad garment absorbs thermal heat transmitted by the user's body. In the alternate preferred embodiment, a plurality of small bores extend through the hip pad to allow for ventilation. These aeration bores allow the heat absorbed by the hip pad to be dissipated into the air. The aeration bores may be positioned in various geometric locations away from the cross-slits without affecting the energy absorbent and dispersion properties of the hip pad.

DESCRIPTION OF THE DRAWINGS

The foregoing features and advantages of the present invention will be readily apparent to those skilled in the art from a review of the following detailed descriptions of the preferred embodiment in conjunction with the accompanying drawings in which.

DETAILED DESCRIPTION OF THE PREFERRED EMBODIMENT

Figure 1:
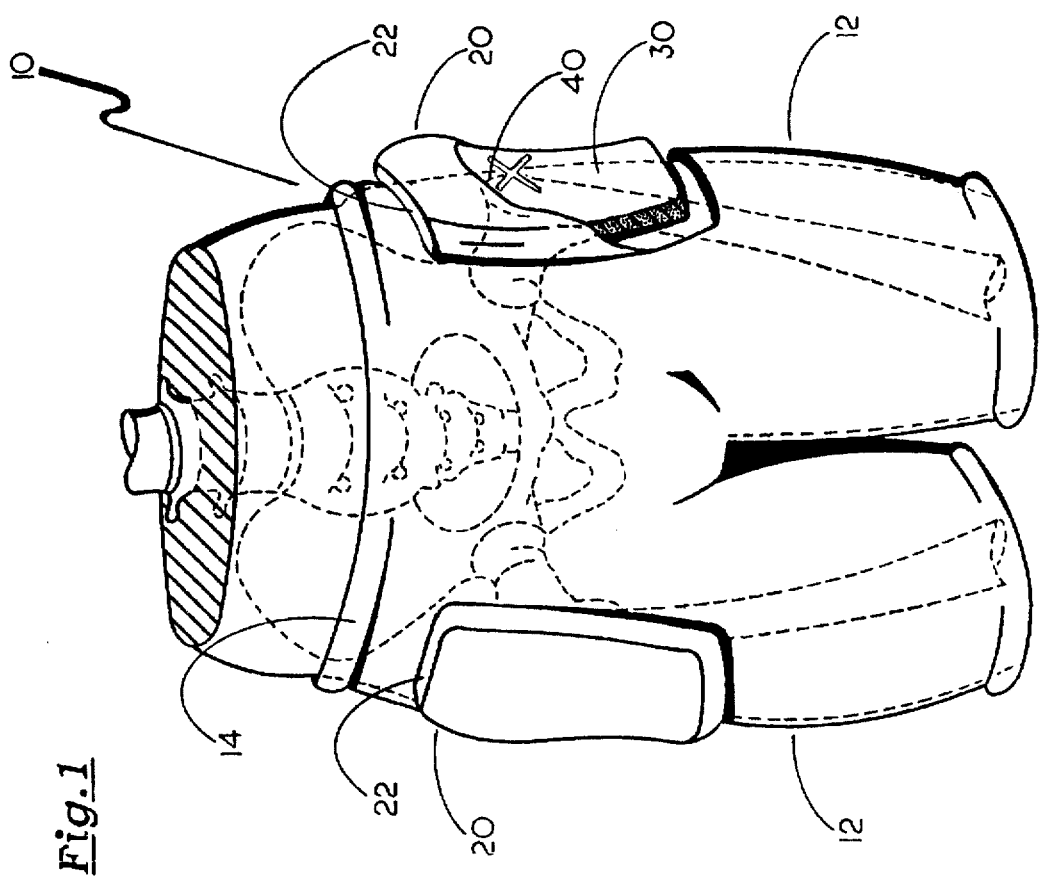
FIG. 1 shows a front view of the form-fitting garment encompassing the human body and skeletal system with a sectioned-away pocket showing the hip pad.

Referring first to FIG. 1, there is indicated generally by numeral 10 a hip protector garment incorporating a preferred embodiment of the present invention. The hip protector garment 10 is made of a stretch fabric such as spandex, one form of which is marketed as Lycra, a trademark of DuPont Chemical, or other form-fitting stretchable fabric. On each side 12 of the hip protector garment 10 is a pocket 20 that retains a foam pad 30. The pockets 20 may be sewn on or otherwise securely attached to the sides. The pockets 20 have an opening 22 that allows insertion or removal of the hip pad 30. In the alternate preferred embodiment, the opening 22 is sewn shut or otherwise securely affixed to the hip protector garment sides 12. An elastic band 14 is preferably attached or sewn around the circumference of the top body encircling opening. Of course, other means for securely holding the hip protector garment 10 above the user's waist may include a drawstring, belt, straps, or other means to securely hold the garment above the waist without deviating from the present invention.

Figure 2:
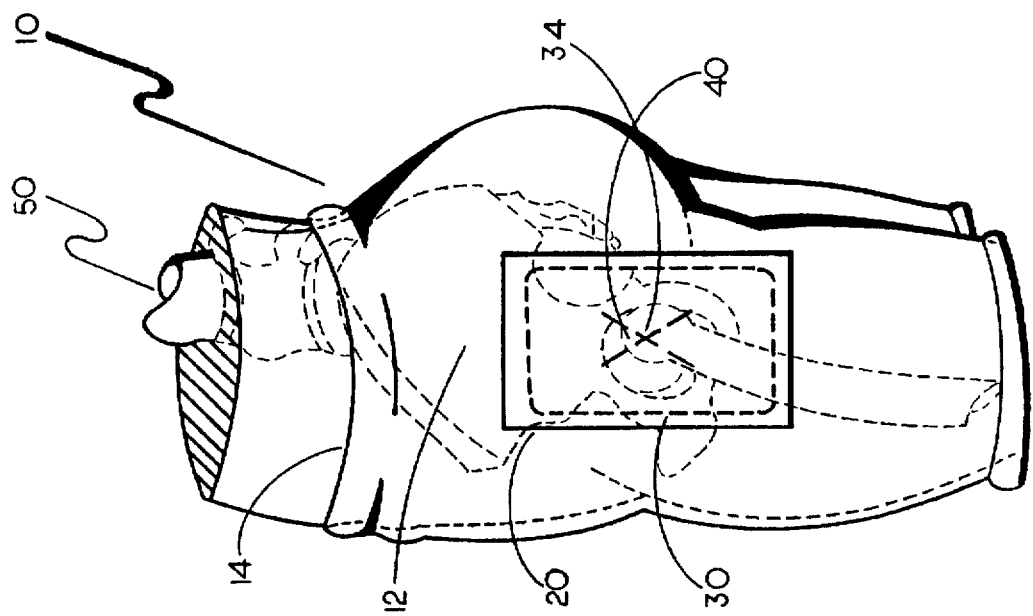
FIG. 2 shows a side view of the hip protector garment of the type shown in FIG. 1.

Referring next to FIG. 2, the pockets are positioned on the garment so that when the hip protector garment is worn by a human subject, the cross-slit 34 extending through the hip pad 30 is created with its apex aligned with the greater trochanter 40 of the human skeletal system 50 of the wearer. A cross-slit 34 extends through the planar surface of the hip pad 30 (see FIG. 3). The center of the cross-slit 34 is approximately centered above the apex of the greater trochanter 40. When a force is applied against the hip pad 30, the cross-slit 34 allows the area of the pad surrounding the greater trochanter region to compress more than the remaining area of the hip pad 30. This action, in turn, disperses the impact force against the pad away from the greater trochanter region. The energy from the forces against the pad are absorbed in the remaining region away from the greater trochanter area, thereby reducing fracture injuries of the greater trochanter region. The pocket 20 is positioned on the garment 10, of various sizes, so that the hip pad 30 automatically aligns with varying body sizes and shapes.

The hip pad 30 is constructed from a resilient polymeric foam material known in the art for absorbing energy from impact forces. In the preferred embodiment, AFP #202, a closed-celled, crosslinked polyethylene, available from American Flexible Products of Chaska, Minn., is used. The AFT #202 foam has the following properties:

| Property | Value |
| --- | --- |
| Density ASTM 3575 ½-inch | 2 pounds per cubic foot |
| Tensile strength--psi | 50 |
| Elongation percent | 180 |
| Tear strength--pounds per inch | 10.2 |
| Compression deflection--psi | 7.8 |
| Compression set percent | 12 |
| K factor | .247 |
| Working temp | −70 to 212° F. |
| Water absorption--psi | .01 |

Figure 3:
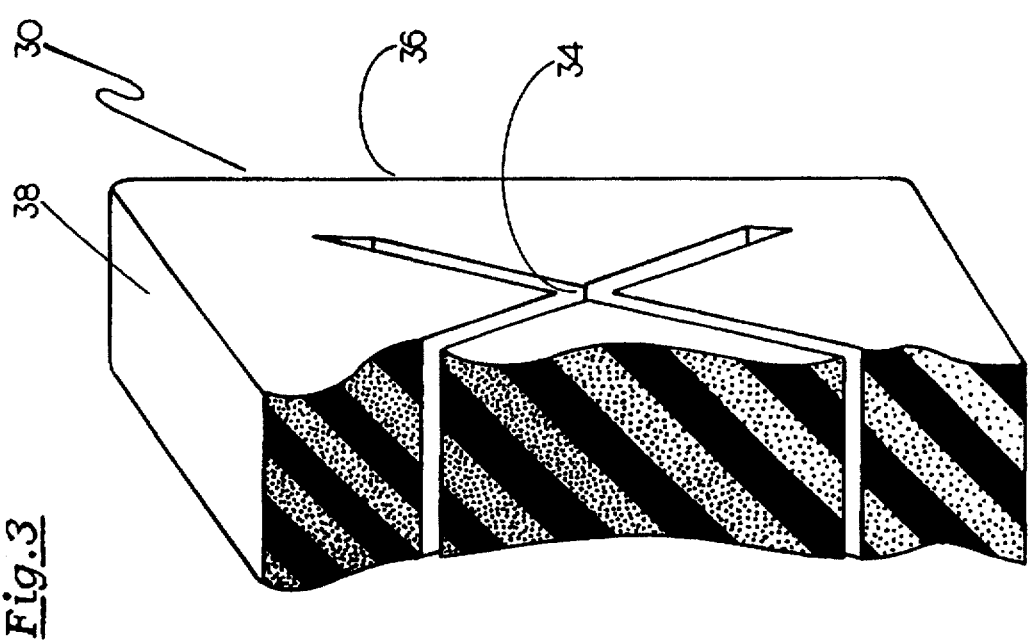
FIG. 3 shows a perspective view of the hip pad sectioned away.

Referring to FIG. 3, the hip pad 30 having the above qualities is generally a rectangular form having long side edges 36 and opposed shorter side edges 38. The rectangle may, for example, be 6.5 inches by 8.5 inches with a thickness of one-half inch. Other sizes may be used while sufficiently protecting the greater trochanter region.

Figure 4:
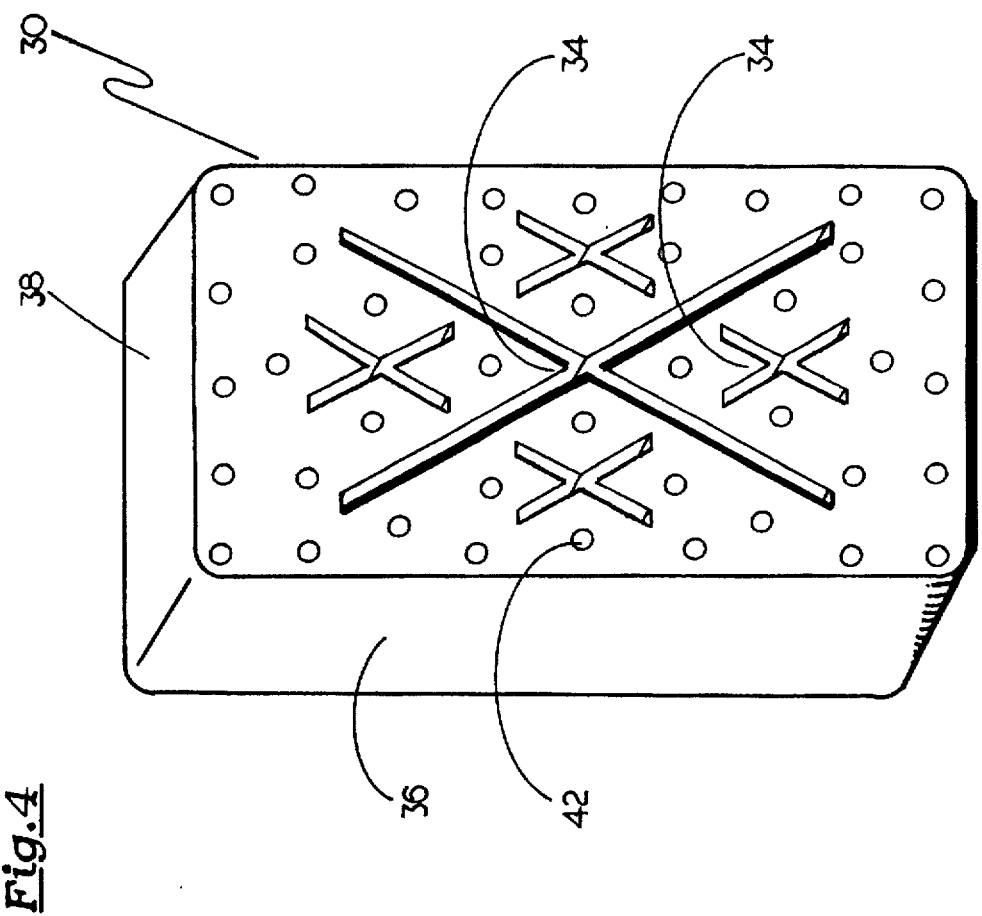
FIG. 4 shows a perspective view of the alternate preferred embodiment of the hip pad of the type shown in FIG. 3.

In the alternate preferred embodiment (see FIG. 4), a plurality of cross-slits 34 are formed around the center of the hip pad 30. The plurality of cross-slits 34 may be arranged in various configurations, with FIG. 4 showing one such configuration. The plurality of cross-slits provides a further means to center a cross-slot 34 with the apex of the greater trochanter. A cross-slot 34 nearest the apex of the greater trochanter compresses more than the other plurality of cross-slits 34, thereby dispersing the energy away from the greater trochanter region. Also, the plurality of slits do not require the hip pad 30 to be exactly aligned with the hip. Shifting of the garment will not affect the effectiveness of the hip pad 30. Without limitation, some of the plurality of slits may extend only partially through the hip pad 30, allowing a greater number of cross-slits in the center portion of the hip pad 30. Through-slits are preferred, however. A plurality of aeration bores 42 may extend through the hip pad 30. These aeration bores 42 may be arranged in various configurations, with FIG. 4 showing one such configuration. The aeration bores 42 dissipate some of the thermal energy absorbed by the hip pad 30 without affecting the absorption and dispersion of energy from an impact to the hip pad 30. The aeration bores 42 provide further flexibility of hip pad 30, increasing the comfort level of the user.

Having described the constructional features of the hip pad and garment for protecting the greater trochanter from impact, the mode of use will now be discussed. The garment and hip pad are primarily designed to be worn by the elderly who are at greater risk of hip fractures. The user may wear the protector garment underneath other clothing, or may be fashioned to be worn without outer garments. The hip pads are placed in the pockets of the garment and the garment is then worn similar to a pair of shorts. The hip pads are flexible and form fitting allowing the user to comfortably wear the hip protector garment 10. While being worn, the placement of the pockets 20 on the garment ensures that the mid-point of the cross-slit 34 will be positioned over the apex of the greater trochanter 40. The garment is form fitting, keeping the hip pad 30 in relatively the same alignment.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different materials and methods and that various modifications both as to the materials and form can be accomplished without departing from the scope of the invention itself.

What is claimed is:

1. An apparatus for decreasing the risk of trauma to the hip joint and greater trochanter region comprising: a garment that rests over the hips having a means to securely hold in place a planar hip pad, said garment including said planar hip pad of uniform cross-sectional thickness and having a geometric center and with at least one slot formed therein and with the midpoint of the slot extending through the said geometric center of said planar hip pad and wherein said garment centers the midpoint of said slot over the greater trochanter region.

2. A device as recited in claim 1 in which the means to securely hold in place said hip pad further comprises form-fitting shorts with pockets positioned on said garment to center said hip pad over said greater trochanter region.

3. A device as recited in claim 1 in which said garment further comprises shorts made of semi-expandable material.

4. A device as recited in claim 1 in which said hip pad further comprises crosslinked polyethylene closed-cell foam having an approximate density of 2 pounds per cubic foot.

5. A device as recited in claim 1 in which said hip pad has a plurality of slots, some of said slots partly extending through said hip pad and those slots passing through said geometric center extending completely through said hip pad, and in alignment with the center of said planar hip pad.

6. A device as recited in claim 5 wherein said hip pad further having at least one bore extending at least partially through said planar hip pad and positioned in a spaced relation to said slot.

* * * * *